(12) United States Patent
Pavliak et al.

(10) Patent No.: US 7,531,633 B2
(45) Date of Patent: May 12, 2009

(54) STAPHYLOCOCCUS ANTIBODIES

(75) Inventors: Viliam Pavliak, Potomac, MD (US); Ali Ibrahim Fattom, Rockville, MD (US)

(73) Assignee: Nabi Biopharmaceuticals, Rockville, MD (US)

( * ) Notice: Subject to any disclaimer, the term of this patent is extended or adjusted under 35 U.S.C. 154(b) by 509 days.

(21) Appl. No.: 11/014,997

(22) Filed: Dec. 20, 2004

(65) Prior Publication Data

US 2005/0118190 A1 Jun. 2, 2005

Related U.S. Application Data

(62) Division of application No. 09/272,359, filed on Mar. 19, 1999, now Pat. No. 6,936,258.

(51) Int. Cl.
*A61K 39/395* (2006.01)
*A61K 39/00* (2006.01)
*A61K 39/40* (2006.01)
*A61K 38/00* (2006.01)
*A61K 35/14* (2006.01)
*A01N 37/18* (2006.01)
*C12P 21/08* (2006.01)
*C07K 16/00* (2006.01)

(52) U.S. Cl. ............... 530/387.1; 530/388.4; 530/388.1; 530/387.3; 530/388.85; 530/388.15; 530/387.5; 514/2; 435/975; 424/130.1; 424/133.1; 424/134.1; 424/139.1; 424/141.1; 424/142.1; 424/150.1; 424/164.1; 424/165.1

(58) Field of Classification Search ................ None
See application file for complete search history.

(56) References Cited

U.S. PATENT DOCUMENTS

| | | | |
|---|---|---|---|
| 4,902,616 A | | 2/1990 | Fournier et al. |
| 5,770,208 A | | 6/1998 | Fattom et al. |
| 5,961,975 A | | 10/1999 | Fattom et al. |
| 5,965,374 A | * | 10/1999 | Herbstritt et al. ............. 435/7.1 |
| 6,045,805 A | | 4/2000 | Moreau |
| 6,194,161 B1 | | 2/2001 | Fattom et al. |
| 6,294,177 B1 | * | 9/2001 | Fattom .................... 424/243.1 |
| 6,355,625 B1 | * | 3/2002 | Pavliak et al. ................. 514/54 |
| 6,936,258 B1 | * | 8/2005 | Pavliak et al. ............ 424/243.1 |
| 7,030,101 B2 | * | 4/2006 | Pavliak et al. ................. 514/54 |
| 7,279,162 B1 | * | 10/2007 | Fischer .................... 424/165.1 |

FOREIGN PATENT DOCUMENTS

| | | | |
|---|---|---|---|
| WO | WO 93/09811 | | 5/1993 |
| WO | WO 98/10788 | | 3/1998 |
| WO | WO 98/28002 | | 7/1998 |
| WO | WO 00/56357 A2 | * | 9/2000 |

OTHER PUBLICATIONS

Fattom et al, Vaccine, 1995, 13/14:1288-1293.*
Fattom et al, Infection and Immunity, 1996, 64/5:1659-1665.*
Lee et al, Infection and Immunity, 1997, 65/10:4146-4151.*
Fattom et al, Infection and Immunity, 1993, 61/3:1023-1032.*
Fattom et al, Infection and Immunity, 1992, 60/2:584-589.*
Casadevall et al, Expert Opin. Biol Ther., 2005, 5/10:1359-1372.*
Projan et al, Current Opinion in Pharmacology, 2006, 6:473-479.*
Bregenholt et al, Expert Opin, Biol. Ther., 2004, 4/3:387-396.*
Karakawa et al., J. Exp. Med. 128/2: 325-340 (1968).
Osawa et al., Biochemistry, 8/8: 3369-3375 (1969).
Kusumoto et al., Bull. Chem. Soc. Jpn. 49/2:533-539, (1976).
Fattom et al., Infection & Immunity 66/10: 4588-4592 (1998).
Gunnarsson et al., Infection & Immunity 45/1: 41-46 (1984).
Ohshima et al., "Cell Surface Antigen of Encapsulated Staphylococcus-Epidermidis SE-360 Protects Mice From Homologous Infection", Zbl. Bakt. Hyg. Series A. vol. 270, pp. 219-227 (1988) XP000939097.
Kojima et al., "Antibody to the Capsular Polysaccharide/Adhesion Protects Rabbits against Catheter-related Bateremia due to Coagulase-Negative Staphylococci", J. of Injec. Diseases, vol. 162, pp. 435-441 (1990) XP000867597.
Tojo et al., "Isolation and Characterization of a Capsular Polysaccharide Adhesin From *Staphyloccus epidermidis*", The Journal of Infectious Diseases, vol. 157, No. 4, Apr. 1988, pp. 713-722.
Timmerman et al., "Characterization of a Proteinaceous Adhesin of *Staphylococcus epidermidis* which Mediates Attachment to Polystyrene", Infection and Immunity, vol. 59, No. 11, Nov. 1991, pp. 4187-4192.
Mack et al., "Characterization of Transposon Mutants of Biofilm-Producing *Staphylococcus epidermidis* Impaired in the Accumulative Phase of Biofilm Production: Genetic Identification of a Hexosamine-Containing Polysaccharide Intercellular Adhesin": Infection and Immunity; vol. 62, No. 8, Aug. 1994, pp. 3244-3253.
Mack et al., "Parallel Induction by Glucose of Adherence and a Polysaccharide Antigen Specific for Plastic Adherent *Staphylococcus epidermidis*: Evidence for Functional Relation to Intercellular Adhesion", Infection and Immunity; vol. 60, No. 5, May 1992, pp. 2048-2057.
Mack et al., "The Intercelluar Adhesin Involved in Biofilm Accumulation of *Staphylococcus epidermidis* is a Linear β-1, 6-Linked Glucosaminoglycan: Purification and Structural Analysis", Bacteriology, vol. 178, No. 1, Jan. 1996, pp. 175-183.
Hussain et al., "A 140-kilodalton Extracellular Protein is Essential for the Accumulation of *Staphylococcus epidermidis* Strains on Surfaces", Infection and Immunology, vol. 65, No. 2, Feb. 1997, pp. 519-524.

* cited by examiner

*Primary Examiner*—N. M Minnifield
(74) *Attorney, Agent, or Firm*—Foley and Lardner LLP

(57) ABSTRACT

A negatively-charged *Staphylococcus* antigen contains amino acids and a N-acetylated hexosamine as a major carbohydrate component. The antigen is common to many coagulase-negative strains of *Staphylococcus*, including *S. epidermidis, S. haemolyticus*, and *S. hominis*. *Staphylococcus* strains that carry the antigen include many clinically significant strains of *Staphylococcus*. The antigen and antibodies to the antigen are useful in kits and assays for diagnosing *Staphylococcus* infection. Vaccines of the antigen and of whole cells that carry the antigen also are disclosed.

13 Claims, 3 Drawing Sheets

STAPHYLOCOCCUS ANTIBODIES

CROSS-REFERENCE TO RELATED PATENT APPLICATIONS

This application is a Divisional Application of U.S. application Ser. No. 09/272,359, filed Mar. 19, 1999, and issued as U.S. Pat. No. 6,936,258, Aug. 30, 2005.

BACKGROUND OF THE INVENTION

The present invention relates to a novel *Staphylococcus* antigen, and to a method for obtaining and using the antigen.

*Staphylococcus* causes several diseases by various pathogenic mechanisms. The most frequent and serious of these diseases are bacteremia and its complications in hospitalized patients. In particular, *Staphylococcus* can cause wound infections and infections associated with catheters and prosthetic devices. Serious infections associated with *Staphylococcus* bacteremia include osteomyelitis, invasive endocarditis and septicemia. The problem is compounded by multiple antibiotic resistance in hospital strains, which severely limits the choice of therapy. In the majority of cases the causative organism is a strain of *S. aureus, S. epidermidis, S. haemolyticus* or *S. hominis*, or a combination of these. The problem with *Staphylococcus* is compounded by multiple antibiotic resistance in hospital strains, which severely limits the choice of therapy.

A *S. aureus* vaccine would provide a solution for the problem of antibiotic resistance. An antigen common to multiple *Staphylococcus* species would enable production of a vaccine containing a single antigen that would be effective against a wide variety of *staph* infections.

SUMMARY OF THE INVENTION

It is therefore an object of the present invention to provide an antigen common to a majority of clinically-significant strains from multiple species of *Staphylococcus*.

It is a further object to provide a vaccine that contains an antigen common to a majority of clinically-significant strains from multiple species of *Staphylococcus*.

It is another object to provide a hyperimmune globulin composition that contains antibodies directed against an antigen common to a majority of clinically-significant strains from multiple species of *Staphylococcus*.

It is a further object of the present invention to provide a whole cell vaccine of cells that carry an antigen that is common to a majority of clinically-significant strains from multiple *Staphylococcus* species, particularly one that is common to the coagulase-negative species of *S. epidermidis, S. haemolyticus* and *S. hominis*.

It is yet another object to provide a kit and assay for diagnosing *Staphylococcus* infection.

In accordance with these and other objects according to the invention, there is provided an isolated *Staphylococcus* antigen that (a) comprises amino acids and a N-acetylated hexosamine in an α configuration, (b) contains no O-acetyl groups detectable by nuclear magnetic resonance spectroscopy, and (3) specifically binds with antibodies to a *Staphylococcus* strain deposited under ATCC 202176.

Also provided is a composition comprising the *Staphylococcus* antigen, and a sterile, pharmaceutically-acceptable carrier therefor. An immunotherapy method comprises a step of administering to a subject an immunostimulatory amount of such a composition.

There also is provided a whole cell vaccine comprising cells from a strain of *Staphylococcus* that carries the antigen.

Also provided is a composition comprising the whole cell vaccine, and a sterile, pharmaceutically-acceptable carrier therefor. The vaccine can be administered to a subject to provide protection against *Staphylococcus* infection.

An immunotherapeutic agent against *Staphylococcus* infection can be prepared by immunizing subjects with a composition according to the invention, collecting plasma from the immunized subjects, and harvesting a hyperimmune globulin that contains antibodies directed against *Staphylococcus* from the collected plasma. The hyperimmune globulin contains antibodies directed against the antigen. An immunotherapy method comprises a step of administering this hyperimmune globulin to a subject.

The present invention also provides a catheter coated with an antigen according to the invention, and a method for preventing adherence of *Staphylococcus* bacteria to a catheter, comprising treating a catheter with antigen according to the invention. In a preferred embodiment, the catheter is an intravenous catheter.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DESCRIPTION OF PREFERRED EMBODIMENTS

Figure 1A:
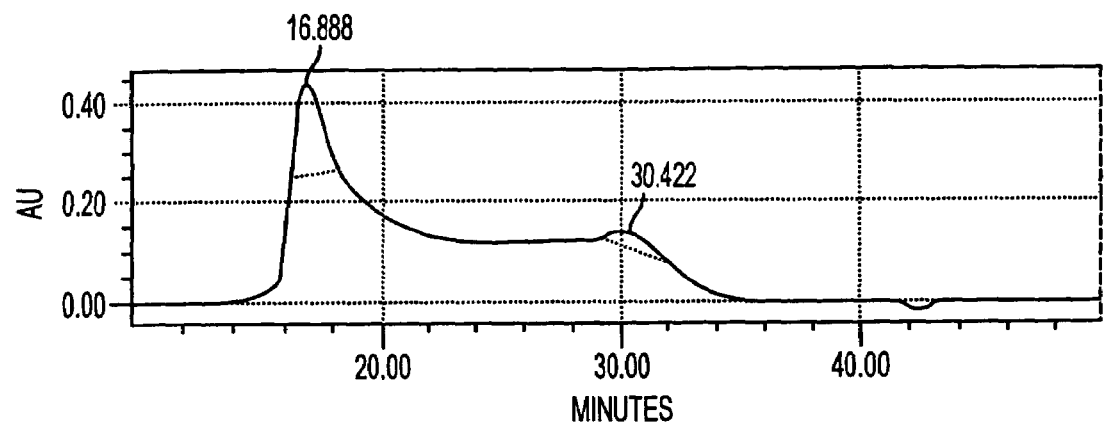
FIGS. 1A and 1B are the chromatographic profile on Superose 6HR for the *Staphylococcus* antigen according to the inventor.

It has been discovered that many clinically-significant isolates of *S. epidermidis, S. haemolyticus,* and *S. hominis* have in common an antigen, herein denoted "the antigen." The antigen represents the basis for a vaccine that provides protection against infection by a large number of clinically-significant *Staphylococcus* isolates. In this regard, a "clinically-significant" isolate is an isolate that is pathogenic.

Notably, the present inventors found that a majority of *Staphylococcus* clinical isolates reacted very strongly with antigen/conjugate antibody sera, and thus were typeable as strains that contain the antigen. More particularly, typing of clinical isolates obtained from various sources has shown that approximately 60% of *S. epidermidis*, 50% of *S. haemolyticus* and 40% of *S. hominis* isolates express the antigen, as determined by slide agglutination. When enzymatic digests of the *S. haemolyticus* and *S. hominis* isolates were subjected to an immunodiffusion assay, all of the isolates tested positive for the presence of the antigen.

Antibodies to the antigen do not cross-react with polysaccharides isolated from any of *S. aureus* Type 5, Type 8, Type 4, or K73 (a Type 5 variant strain). The antigen therefore is specific, that is, it produces a single band only with antiserum from homologous strains.

The antigen can be obtained in recoverable amount, from certain *Staphylococcus* isolates cultured pursuant to the protocols described herein, in substantially pure form. In particular, purified antigen contains less than 1% nucleic acids. A "recoverable" amount in this regard means that the isolated amount of the antigen is detectable by a methodology less sensitive than radiolabeling, such as immunoassay, and can be subjected to further manipulations involving transfer of the antigen per se into solution.

To obtain the antigen, an isolate according to the invention first is fermented in a modified Columbia Broth supplemented with and 4% NaCl. Following fermentation, cells are killed and then centrifuged to separate the cells from the supernatant.

Antigen is extracted from cell paste. Some of the antigen is present in the supernatant, but the amount is insignificant as compared to the amount found in the cell paste. Because of the low yield, and the risk of hexose contamination from the media, extraction from supernatant is not preferred.

A suspension of the cell paste is treated with pronase, lysostaphin, DNase and RNase. The suspension is made 10% in trichloroacetic acid (TCA) and incubated at 60° C. After centrifugation, the supernatant is neutralized with 1M NaOH to pH 7.0, followed by sequential precipitation with 25-75% cold ethanol/$CaCl_2$ to remove nucleic acids and high molecular weight proteins and then precipitate antigen-containing material.

The crude precipitate is dissolved in water and residual ethanol is removed by dialysis. Residual teichoic acid is removed by anion-exchange chromatography. Fractions are tested by capillary precipitation with antibodies specific for the antigen to determine antigen-containing fractions, which are pooled, dialyzed, lyophilized and treated with lysozyme to digest residual peptidoglycan. The enzyme-treated crude antigen-containing fraction is resuspended and rechromatographed on an anion-exchange column in a 0.1-0.25 M NaCl linear gradient in tris-HCl buffer, pH 7.0. Phosphorus-negative and antigen-positive fractions, as determined by colorimeteric assay and capillary precipitation with monospecific antiserum, respectively, are pooled, dialyzed against water and lyophilized. Most of the antigen elutes at 0.2 M NaCl. The crude antigen is further purified by column chromatography, and antigen-containing fractions are pooled to produce substantially pure antigen.

Purified antigen produces a single precipitin band when reacted with whole cell antisera in a double immunodiffusion assay. Immunoelectrophoresis of purified antigen and elution pattern on ion-exchange column during the purification process indicate a negatively-charged molecule.

Figure 1B:
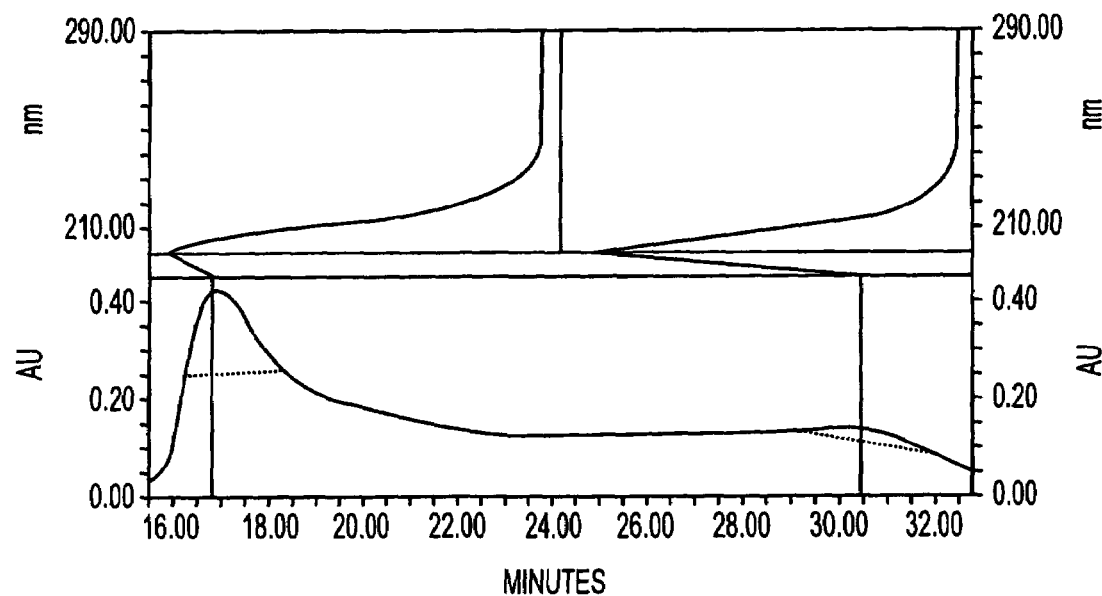

Both substantially pure antigen and antigen repurified by reverse phase chromatography on a C18 column show a polydisperse profile on a Superose 6HR column (FIG. 1). Both contain less than 1% of nucleic acids. No hexoses, phosphorus or O-acetyl groups are detected by colorimetric assays. Purified antigen does not stain in Coomasie blue SDS-PAGE.

Analysis of purified antigen by gas liquid chromatography-mass spectroscopy (GLC-MS) shows the presence of GlcNAc as a major glycosyl component. It is sensitive to mild acid, indicating that the GlcNAc residues are not linked by glycosidic bonds. The antigen is resistant to the action of proteolytic enzymes.

Figure 2A:
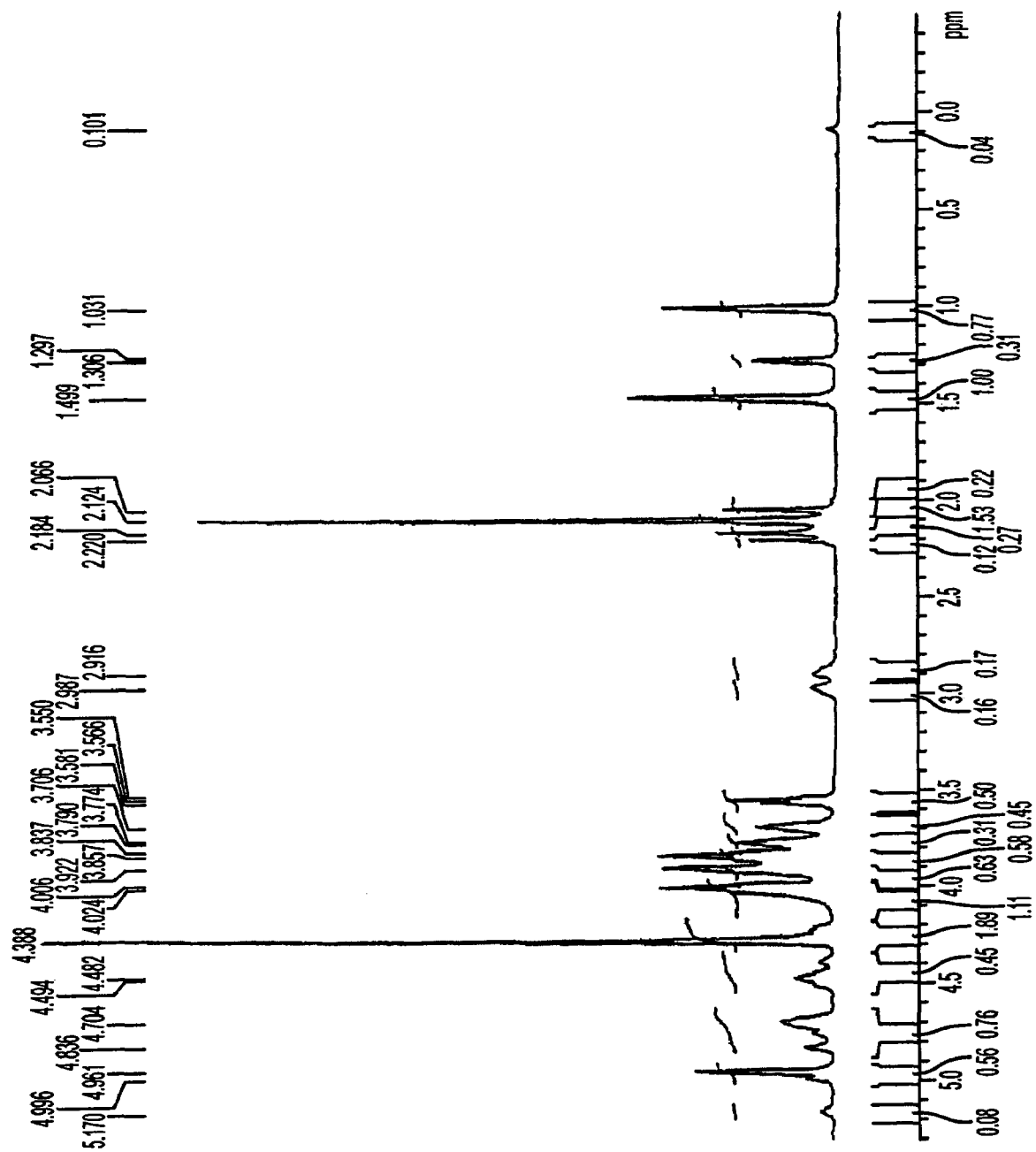
FIGS. 2A and 2B are NMR spectra for the *Staphylococcus* antigen according to the invention.
Figure 2B:
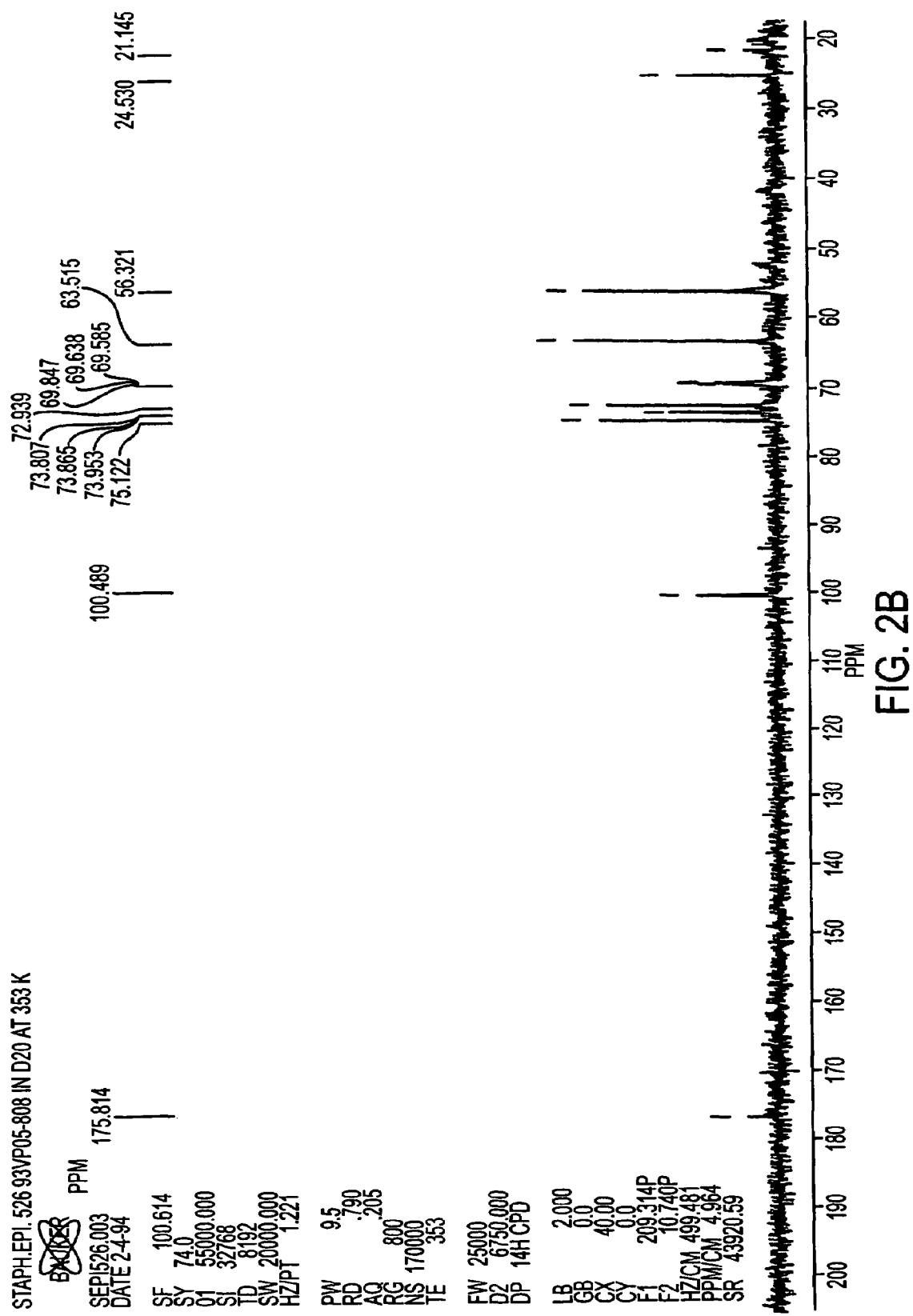

The presence of GlcNAc is confirmed by 1H-NMR and 13C-NMR spectroscopy of the antigen, which indicate one anomeric signal at $\delta$ 4.88 and $\delta$ 100.48 ppm, respectively (see FIGS. 2a and 2b). NMR spectroscopy also confirms the absence of O-acetyl groups. This absence of O-acetylation is in distinct contrast to other Staphylococcus antigens, such as Type 5 and Type 8, which contain from 20-80% O-acetylation.

A small value of JH1,H2 (<1.0 Hz) indicates an $\alpha$ configuration for the glucosamine, which is confirmed by a measurement of c=173 Hz for the JC,H coupling constant. Signals at $\delta$ 24.860 ppm (NAac-$CH_3$) and $\delta$ 176.814 ppm (NAc-CO) in the 13C NMR spectrum suggest that the glucosamine is N-acetylated, so that the carbohydrate portion of the antigen is postulated to be 2-acetamido-2-deoxy-$\alpha$-D-glucopyranoside.

Amino acid analysis of the antigen shows the presence of serine, alanine, aspartic acid/asparagine, valine, and threonine in molar ratios of approximately 39:25:16:10:7. Amino acids constitute about 32% by weight of the antigen molecule.

A comparison of the NMR spectra for the antigen with the NMR spectra for each of the Type 5 and Type 8 S. aureus antigens and with the NMR spectra for the 336 antigen disclosed in U.S. Pat. No. 5,770,208 shows that it is chemically distinct from these antigens. The structures of Types 5 and 8 polysaccharide antigens have been elucidated by Moreau et al., Carbohydr. Res. 201:285 (1990); and Fournier et al., Infect. Imm. 45:87 (1984). Both have FucNAcp in their repeat unit as well as ManNAcA which can be used to introduce a sulfhydryl group. The structures are as follows:

Type 5:

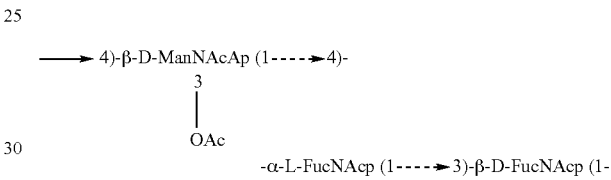

Type 8:

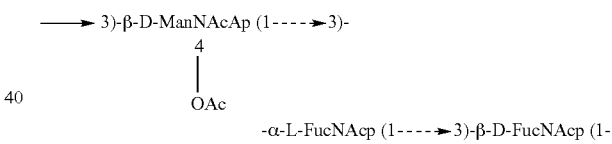

By contrast, the antigen according to the present invention has glucosamine as its main carbohydrate component. Unlike the Type 5 and Type 8 S. aureus antigens, it contains amino acids.

Induction of bacteremia in mammals requires extremely high numbers of organisms or some previous maneuver to lower the host resistance. In vitro phagocytosis, however, can be studied as a correlate of protective immunity in vivo. In this model, the ability of antigen-specific monoclonal and polyclonal antibodies to opsonize Staphylococcus isolates in vitro is measured by phagocytosis, according to the method described in Kojima et al., Infect. Dis. Immun. 58: 2367-2374 (1990). In vitro opsonophagocytosis assays are recognized in the field as being predictive of efficacy as a vaccine. For example, Fischer et al. discloses a correlation between functional antibody determined with an in vitro opsonic assay and in vivo activity. J. Inf. Dis. 169: 324-9 (1994).

Antibodies induced by a vaccine containing the antigen facilitate type-specific phagocytosis. The in vitro phagocytosis assays thus indicate that antibodies to the antigen are protective against infection by Staphylococcus strains that carry the antigen. A vaccine based on the antigen can be used to protect against infection from a majority of clinical Staphylococcus strains. In vivo results obtained with the mouse lethality model and the mouse bacteremia model are consistent with results of in vitro opsonophagocytosis assays, and show that antibodies to antigen conjugates lowered mortality and bacteremia in mice challenged with strains of *Staphylococcus* that carry the antigen.

Preferably, a composition of the antigen or of whole cells containing the antigen according to the present invention "consists essentially of" the antigen, or cells that contain the antigen. In this context, the phrase "consists essentially of" means that the composition does not contain any material that interferes with elicitation of an immune response to the antigen (and to other antigens, if present) when the composition is administered to a subject as a vaccine, or with the antigen-antibody coupling characteristic of a diagnostic assay when the antigen is used in diagnosis.

The antigen according to the invention is useful in the production of diagnostic assays for detecting the presence of *Staphylococcus* antigen and/or anti-*Staphylococcus* antibody in a sample. The antigen, or antibody specific to the antigen, alone or in combination with other *Staphylococcus* antigens or antibodies, is mixed with a sample suspected of containing *Staphylococcus* antigen or antibody and monitored for antigen-antibody binding. The antigen or antibody is labelled with a radioactive or enzyme label. In a preferred embodiment, antigen or antibody is immobilized on a solid matrix such that the antigen or antibody are accessible to complementary antibody or antigen contacting a surface of the matrix. The sample then is brought into contact with the surface of the matrix, and the surface is monitored for antigen-antibody binding.

For example, the antigen or antibody can be used in an enzyme-linked immunosorbent assay (ELISA), in which antigen or antibody are bound to a solid phase and an enzyme-antibody or enzyme-antigen conjugate is used to detect and/or quantify antibody or antigen present in a sample. Alternatively, a western blot assay can be used in which solubilized and separated antigen(s) is bound to nitrocellulose paper. The antibody then is detected by an enzyme or label-conjugated anti-immunoglobulin (Ig), such as horseradish peroxidase-Ig conjugate by incubating the filter paper in the presence of a precipitable or detectable substrate. Western blot assays have the advantage of not requiring purity greater than 50% for the desired antigen(s). Descriptions of ELISA and western blot techniques are found in Chapters 10 and 11 of Ausubel, et al. (eds.), CURRENT PROTOCOLS IN MOLECULAR BIOLOGY, John Wiley and Sons (1988), the entire contents of which are hereby incorporated by reference.

For use in a vaccine, it is preferable to conjugate the antigen to an immunocarrier, usually a polypeptide or protein, to improve the interaction between T and B cells for the induction of an immune response against the antigen. This is particularly important for vaccines intended for use in patients with reduced resistance. An immunocarrier enhances immunogenicity both for active immunization and for preparing high-titered antisera in volunteers for passive immunization. Suitable immunocarriers according to the present invention include tetanus toxoid, diphtheria toxoid, *Pseudomonas aeruginosa* Exotoxin A or its derivatives, recombinantly-produced non-toxic mutant strains of exotoxin A, as described, for example, in Fattom et al., *Inf. and Imm.* 61: 1023-1032 (1993), as well as other proteins commonly used as immunocarriers.

In order to conjugate the antigen to a carrier protein, the antigen is first derivatized. Various methods can be used to derivatize antigen and covalently link it to an immunocarrier. Activated carboxylate groups of the antigen can be derivatized with ADH, cystamine or PDPH, and then the antigen can be coupled to a carrier protein either by a carbodiimide-mediated reaction of the partially-amidated antigen to a carboxylate group on the carrier protein or by disulfide interchange of thiolated antigen with an SPDP-derivatized carrier protein.

Hydroxyl groups on the antigen can be activated using cyanogen bromide or 1-cyano-4-dimethylamino-pyridinium tetrafluoroborate, and then the antigen can be derivatized with the six carbon bifunctional spacer adipic acid dihydrazide (ADH), according to techniques known in the art, according to the method of Kohn et al. *FEBS Lett.* 154: 209:210 (1993). This material then is linked to diphtheria toxoid (Dtd), recombinant exoprotein A from *Pseudomonas aeruginosa* (rEPA) tetanus toxoid (TTd) or another suitable carrier protein by 1-ethyl-3-(3-dimethylaminopropyl) carbodiimide (EDAC). The resulting conjugates can be separated from unreacted antigen by size exclusion chromatography. Regardless of the method used to conjugate the antigen to the carrier protein, covalent linking of the antigen to the carrier protein significantly enhances the immunogenicity of the antigen, and results in increased levels of antibodies to the antigen after both the first and second boost in mice.

Preferably, the antigen or antigen conjugate is administered without an adjuvant in order to avoid adjuvant-induced toxicity. If an adjuvant is used, it is preferred to use one which promotes the protective IgG subtype 2 antibodies. Typical adjuvants include aluminum hydroxide, complete Freund's adjuvant (CFA) and incomplete Freund's adjuvant (IFA). Dextran sulfate has been shown to be a potent stimulator of $IgG_2$ antibody against staphylococcal cell surface antigens, and also is suitable as an adjuvant.

The present invention also relates to the use of the antigen to produce polyclonal antibodies or monoclonal antibodies (mouse or human) that bind to or neutralize *Staphylococcus* strains that carry the antigen. Protocols for producing these antibodies are described in Ausubel, et al. (eds.), *Molecular Cloning: A Laboratory Manual*, Cold Spring Harbor Laboratory, (Cold Spring Harbor, N.Y.)., Chapter 11; in METHODS OF HYBRIDOMA FORMATION 257-271, Bartal & Hirshaut (eds.), Humana Press, Clifton, N.J. (1988); in Vitetta et al., *Immunol. Rev.* 62:159-83 (1982); and in Raso, *Immunol. Rev.* 62:93-117 (1982).

Inoculum for polyclonal antibody production typically is prepared by dispersing the antigen-immunocarrier in a physiologically-tolerable diluent such as saline, to form an aqueous composition. An immunostimulatory amount of inoculum, with or without adjuvant, is administered to a mammal and the inoculated mammal is then maintained for a time period sufficient for the antigen to induce protecting anti-antigen antibodies. Boosting doses of the antigen-immunocarrier may be used in individuals that are not already primed to respond to the antigen.

Antibodies can include antibody preparations from a variety of commonly used animals, e.g., goats, primates, donkeys, swine, rabbits, horses, hens, guinea pigs, rats, and mice, and even human antibodies after appropriate selection, fractionation and purification. Animal antisera may also be raised by inoculating the animals with formalin-killed strains of *Staphylococcus* that carry the antigen, by conventional methods, bleeding the animals and recovering serum or plasma for further processing.

The antibodies induced in this fashion can be harvested and isolated to the extent desired by well known techniques, such as by alcohol fractionation and column chromatography, or by immunoaffinity chromatography; that is, by binding antigen to a chromatographic column packing like Sephadex™, passing the antiserum through the column, thereby retaining specific antibodies and separating out other immunoglobulins (IgGs) and contaminants, and then recovering purified antibodies by elution with a chaotropic agent, optionally followed by further purification, for example, by passage through a column of bound blood group antigens or other non-pathogen species. This procedure may be preferred when isolating the desired antibodies from the sera or plasma of humans that have developed an antibody titer against the pathogen in question, thus assuring the retention of antibodies that are capable of binding to the antigen. They can then be used in preparations for passive immunization against strains of Staphylococcus that carry the antigen.

A monoclonal antibody composition contains, within detectable limits, only one species of antibody combining site capable of effectively binding to the antigen. Suitable antibodies in monoclonal form can be prepared-using conventional hybridoma technology.

To form hybridomas from which a monoclonal antibody composition of the present invention is produced, a myeloma or other self-perpetuating cell line is fused with lymphocytes obtained from peripheral blood, lymph nodes or the spleen of a mammal hyperimmunized with the antigen. It is preferred that the myeloma cell line be from the same species as the lymphocytes. Splenocytes are typically fused with myeloma cells using polyethylene glycol 1500. Fused hybrids are selected by their sensitivity to HAT. Hybridomas secreting the antibody molecules of this invention can be identified using an ELISA.

A Balb/C mouse spleen, human peripheral blood, lymph nodes or splenocytes are the preferred materials for use in preparing murine or human hybridomas. Suitable mouse myelomas for use in the present invention include the hypoxanthine-aminopterin-thymidine-sensitive (HAT) cell lines, a preferred mycloma being P3X63-Ag8.653. The preferred fusion partner for human monoclonal antibody production is SHM-D33, a heteromyeloma available from ATCC, Manassas, VA under the designation CRL 1668.

A monoclonal antibody composition of the present invention can be produced by initiating a monoclonal hybridoma culture comprising a nutrient medium-containing a hybridoma that secretes antibody molecules of the appropriate specificity. The culture is maintained under conditions and for a time period sufficient for the hybridoma to secrete the antibody molecules into the medium. The antibody-containing medium is then collected. The antibody molecules then can be isolated further by well known techniques.

Media useful for the preparation of these compositions are both well known in the art and commercially available, and include synthetic culture media, inbred mice and the like. An exemplary synthetic medium is Dulbecco's Minimal essential medium supplemented with 20% fetal calf serum. An exemplary inbred mouse strain is the Balb/c.

Other methods of preparing monoclonal antibody compositions are also contemplated, such as interspecies fusions, since it is primarily the antigen specificity of the antibodies that affects their utility in the present invention. Human lymphocytes obtained from infected individuals can be fused with a human myeloma cell line to produce hybridomas which can be screened for the production of antibodies that recognize the antigen. More preferable in this regard, however, is a process that does not entail the use of a biological sample from an infected human subject. For example, a subject immunized with a vaccine as described herein can serve as a source for antibodies suitably used in an antibody composition within the present invention.

In a particularly preferred embodiment, monoclonal antibodies are produced to the antigen using methods similar to those described for type-specific antibodies to S. aureus Type 5 and Type 8. The purified monoclonal antibodies are characterized by bacterial agglutination assays using a collection of clinical isolates.

The monoclonal and polyclonal antibody compositions produced according to the present description can be used by passive immunization to induce an immune response for the prevention or treatment of infection by strains of Staphylococcus that carry the antigen. In this regard, the antibody preparation can be a polyclonal composition. Such a polyclonal composition includes antibodies that bind to the antigen, and additionally may include antibodies that bind to the antigens that characterize other strains of Staphylococcus. The polyclonal antibody component can be a polyclonal antiserum, preferably affinity purified, from an animal which has been challenged with the antigen, and possibly also with other Staphylococcus antigens. Alternatively, an "engineered oligoclonal" mixture may be used, which is a mixture of monoclonal antibodies to the antigen, and monoclonal antibodies to other Staphylococcus antigens.

In both types of mixtures, it can be advantageous to link antibodies together chemically to form a single polyspecific molecule capable of binding to the antigen and to antigens characteristic of other strains of Staphylococcus. One way of effecting such a linkage is to make bivalent $F(ab')_2$ hybrid fragments by mixing two different $F(ab')_2$ fragments produced, e.g., by pepsin digestion of two different antibodies, reductive cleavage to form a mixture of Fab' fragments, followed by oxidative reformation of the disulfide linkages to produce a mixture of $F(ab')_2$ fragments including hybrid fragments containing a Fab' portion specific to each of the original antigens. Methods of preparing such hybrid antibody fragments are disclosed in Feteanu, LABELED ANTIBODIES IN BIOLOGY AND MEDICINE 321-23, McGraw-Hill Int'l Book Co. (1978); Nisonoff, et al., Arch Biochem. Biophys. 93: 470 (1961); and Hammerling, et al., J. Exp. Med. 128: 1461 (1968); and in U.S. Pat. No. 4,331,647.

Other methods are known in the art to make bivalent fragments that are entirely heterospecific, e.g., use of bifunctional linkers to join cleaved fragments. Recombinant molecules are known that incorporate the light and heavy chains of an antibody, e.g., according to the method of Boss et al., U.S. Pat. No. 4,816,397. Analogous methods of producing recombinant or synthetic binding molecules having the characteristics of antibodies are included in the present invention. More than two different monospecific antibodies or antibody fragments can be linked using various linkers known in the art.

An antibody component produced in accordance with the present invention can include whole antibodies, antibody fragments, or subfragments. Antibodies can be whole immunoglobulin of any class, e.g., IgG, IgM, IgA, IgD, IgE, chimeric antibodies or hybrid antibodies with dual or multiple antigen or epitope specificities, or fragments, e.g., $F(ab')_2$, Fab', Fab and the like, including hybrid fragments, and additionally includes any immunoglobulin or any natural, synthetic or genetically engineered protein that acts like an antibody by binding to a specific antigen to form a complex. In particular, Fab molecules can be expressed and assembled in a genetically transformed host like E. coli. A lambda vector system is available thus to express a population of Fab's with a potential diversity equal to or exceeding that of subject generating the predecessor antibody. See Huse, W. D., et al., Science 246: 1275-81 (1989).

The antigen according to the present invention can be the active ingredient in a composition, further comprising a pharmaceutically acceptable carrier for the active ingredient, which can be used as a vaccine to induce a cellular immune response and/or production in vivo of antibodies which combat *Staphylococcus* infection. In this regard, a pharmaceutically acceptable carrier is a material that can be used as a vehicle for administering a medicament because the material is inert or otherwise medically acceptable, as well as compatible with the active agent, in the context of vaccine administration. In addition to a suitable excipient, a pharmaceutically acceptable carrier can contain conventional vaccine additives like diluents, adjuvants, antioxidants, preservatives and solubilizing agents.

In an alternative embodiment, cells that carry the antigen are used in a whole cell vaccine. Cells that carry the antigen can be identified and selected for use in the whole cell vaccine by using antibodies to a strain known to carry the antigen, and more preferably by using monoclonal antibodies to isolated antigen as described herein. In this regard, a simple slide agglutination experiment in which antibodies to the antigen are mixed with cells can be used.

Deposited strain ATCC 202176 is a representative strain of *Staphylococcus* that carries the antigen, and it can be used to produce antibodies useful in identifying other strains that carry the antigen. It is not, however, necessary to use the deposited strain in order to produce either the antigen, the whole cell vaccine or antibodies useful in identifying other cells that carry the antigen. ATCC 202176 merely provides one immunologic means of identifying such cells.

As described for purified antigen vaccine above, the whole cell vaccine also comprises a pharmaceutically acceptable carrier. The whole cell vaccine also optionally may contain conventional vaccine additives like diluents, adjuvants, antioxidants, preservatives and solubilizing agents. In a preferred embodiment, the whole cell vaccine contains only cells which carry the antigen, and does not include cells from strains of *Staphylococcus* that do not carry the antigen.

Vaccines according to the invention can be administered to a subject not already infected with *Staphylococcus*, thereby to induce a *Staphylococcus*-protective immune response (humoral or cellular) in that subject. Alternatively, vaccines within the present invention can be administered to a subject in which *Staphylococcus* infection already has occurred but is at a sufficiently early stage that the immune response produced to the vaccine effectively inhibits further spread of infection.

By another approach, a vaccine of the present invention can be administered to a subject who then acts as a source for globulin, produced in response to challenge from the specific vaccine ("hyperimmune globulin"), that contains antibodies directed against *Staphylococcus*. A subject thus treated would donate plasma from which hyperimmune globulin would then be obtained, via conventional plasma-fractionation methodology, and administered to another subject in order to impart resistance against or to treat *Staphylococcus* infection. Hyperimmune globulins according to the invention are particularly useful for immune-compromised individuals, for individuals undergoing invasive procedures or where time does not permit the individual to produce his own antibodies in response to vaccination.

Similarly, monoclonal or polyclonal anti-*Staphylococcus* antibodies produced according to the present invention can be conjugated to an immunotoxin, and administered to a subject in whom *Staphylococcus* infection already has occurred but has not become widely spread. To this end, antibody material produced pursuant to the present description would be administered in a pharmaceutically acceptable carrier, as defined herein.

The present invention is further described by reference to the following, illustrative examples.

EXAMPLE 1

Fermentation of *Staphylococcus*

ATCC 202176, a strain of *S. epidermidis* that carries the antigen, was fermented in a 50-liter fermentor in Columbia Broth supplemented with and 4% NaCl. The fermentation was started with one liter of a 16 hour old seed culture. Cells were fermented for 24 hours with low aeration (1 v.v.m.) and mild agitation (200 rpm) at 37° C. Following fermentation, cells were killed with 2% final concentration of phenyl to ethanol (1:1) and then centrifuged to separate the cells from the supernatant.

Cells to be used as a vaccine to prepare whole cell antiserum were 3% formalin-fixed overnight at room temperature. Cells for purification of antigen were killed by adding phenylethanol (1:1, vol/vol) to the fermentor to a final concentration of 2%, and mixing slowly for 0.2 hours at 15-20° C. No viable cells were detected after this treatment. The cells then were harvested by centrifugation at 14,500×g and stored at −70° C. until use.

EXAMPLE 2

Preparation of Whole Cell Antiserum

Formalin-fixed cells from Example 1 were adjusted at $OD_{540\ nm}=1$ and were injected intravenously into rabbits. No adjuvant was used. Rabbits were bled at weekly and positive whole cell serum was collected and pooled. IgG was purified from whole cell serum by a protein G affinity column.

EXAMPLE 3

Purification of Antigen

Antigen was extracted from cell paste. A suspension of the cell paste (0.5 g/ml) was treated for 4 hours at 37° C. with pronase (1 mg/g of cells) and then with lysostaphin (175 U/g of cells), DNase and RNase (0.1 mg/g of each) and then stored overnight at 4° C. The suspension was made 10% in trichloroacetic acid (TCA) and incubated for 4 hours at 60° C. After centrifugation, the supernatant was neutralized with 1M NaOH to pH 7.0, followed by sequential precipitation with 25-75% cold ethanol in the presence of 10 mM $CaCl_2$. Nucleic acids and high molecular weight proteins were precipitated from neutralized supernatant by adjusting it to 25% ethanol and incubating at 4° C. for 4 hours. After centrifugation, the supernatant was adjusted to 75% ethanol and incubated at 4° C. for 4-12 hours to precipitate antigen-containing material.

The precipitate containing the crude antigen was dissolved in water and residual ethanol was removed by dialysis. The dialyzed material was adjusted to 0.01M Tris-HCl pH 7.0, 0.3 M NaCl and residual teichoic acid was' removed by anion-exchange chromatography on a Q-Sepharosec® column in flow through mode with 0.01 Tris-HCl pH 7.0, 0.3 M NaCl. Fractions were tested by capillary precipitation with antibodies specific for the antigen to determine antigen-containing fractions. Antigen-containing fractions were dialyzed against water (3.times.5 L), lyophilized and treated with lysozyme (0.5 mg/g cell paste) for 3 hours at 37.degree. C. to digest residual peptidoglycan. The enzyme-treated, crude antigen-containing fraction was resuspended in 0.01 M in Tris-HCl pH 7.0 and rechromatographed on a Q-Sepharose® column in 0.1-0.25 M NaCl linear gradient. Phosphorus-negative and antigen-positive fractions, as determined by colorimetric assay and capillary precipitation with monospecific antiserum from Example 2, respectively, were pooled, dialyzed against water and lyophilized. Most of the antigen eluted at 0.2 M NaCl. The crude antigen was further purified on a Sepharose® CL6B column to obtain substantially pure antigen. Antigen-containing fractions were pooled, dialyzed against water and freeze-dried.

EXAMPLE 4

Characterization of Antigen

Analysis of purified antigen by GLC-MS showed the presence of GlcNAc as a major glycosyl component. This was confirmed by 1H-NMR and 13C-NMR spectroscopy of the antigen, which indicated one anomeric signal at $\delta$ 4.88 and $\delta$ 100.48 ppm, respectively. The presence of a single anomeric signal connotes the presence of monosaccharide as a major component. Signals corresponding to O-acetyl groups are not found.

A small value of JH1,H2 (<1.0 Hz) indicated an $\alpha$ configuration for the carbohydrate, which was confirmed by a measurement of c=173 Hz for the JC,H coupling constant. Signals at $\delta$ 24.860 ppm (NAc-CH$_3$) and $\delta$ 176.814 ppm (NAc-CO) in 13C NMR indicated that the glucosamine was N-acetylated, making the carbohydrate portion of the antigen 2-acetamido-2-deoxy-$\alpha$-D-glucopyranoside. Other C13-NMR spectrum signals appear at $\delta$ 75.122, 73.953, 73.865, 73.807, 72.939, 69.847, 69.638, 69.585, 63.515, and 56.321, respectively.

Amino acid analysis of the antigen showed the presence of serine, alanine, aspartic acid/asparagine, valine, and threonine in molar ratios of approximately 39:25:16:10:7. Amino acids constituted about 32% by weight of the antigen molecule.

The mobility of purified antigen upon immunoelectrophoresis (IEF) indicated the presence of negatively-charged groups. The purified antigen did not contain neutral sugars as detected by the phenyl sulfuric assay.

EXAMPLE 5

Preparation of Antigen-immunocarrier Conjugates

Purified antigen was partially depolymerized by hydrolysis in 50 mM acetic acid at 100° C. for 30 minutes, or at 80° C. for 90 minutes. The reaction mixture was freeze-dried and acetic acid was removed lyophilization. A partially hydrolyzed antigen was dissolved in 0.5 M ADH to its final concentration of 5 mg/mL and pH was adjusted to 5.6 with 0.1 M HCl. An antigen solution was made 100 mM EDAC by adding EDAC (as a powder) and pH was maintained at 5.6 with 0.1 M HCl for 1 hour. The reaction mixture then was dialyzed against 0.2 M NaCl (1×), then desalted on a Sephadex G25 column (2.6×30 cm) and freeze-dried. The amount of ADH incorporated into antigen was determined calorimetrically by trinitrobenzene sulfonic acid (TNBS) assay using ADH as a standard.

ADH-derivatized antigen (10 mg) was dissolved in 1795 µL of 0.1M MES buffer pH 5.6 and 205 µL of rEPA solution (48 mg/mL) representing 10 mg of rEPA was added. The reaction mixture was made 100 mM EDAC by adding EDAC (as a powder) and mixture was stirred at room temperature for 60 minutes. The reaction was stopped by bringing the pH to 7.0 with 1M MES-sodium salt (pH 9.21). Pure conjugate was obtained by size exclusion chromatography on Sephacryl S-300 column eluted with PBS. The amount of antigen and protein in the conjugate was determined by competitive ELISA and Coomasie Blue assay (Pierce) using the corresponding antigen or BSA as standards. The similar procedure was used to prepare antigen-Dtd conjugate.

EXAMPLE 6

Preparation of Antisera to Antigen-immunocarrier Conjugates

White female New Zealand rabbits were immunized by subcutaneous injection with 50 µg of antigen-immunocarrier conjugate prepared according to Example 5 on days 0, 14 and 28. The first injection was given with an equal volume of complete Freund's adjuvant (CFA) and subsequent injections were given with incomplete Freund's adjuvant (IFA). Test bleeds taken from rabbits were monitored for the presence of precipitating rabbit antibodies specific to the antigen with which they were immunized. Further injections were given as needed to boost the titer.

Rabbits were bled to obtain high-titered rabbit antisera that contained antibodies specific to the antigen with which they were immunized. The antibodies were able to mediate killing of cells carrying the antigen by HL 60 in the presence of complement. Rabbits immunized with antigen-rEPA or antigen Dtd conjugates were also able to elicit antigen specific antibodies. These antibodies gave precipitates with the antigen in capillary.

Purified conjugate sera IgG was shown to contain 16.0 mg/ml total IgG by ELISA and 1.54 mg/ml antigen-specific IgG by ELISA. Conjugate IgG was used in opsonophagocytosis assays to evaluate the ability of the specific antibodies to mediate opsonophagocytosis of corresponding *Staphylococcus* bacteria by HL-60 cells in in vitro assays, and in animal models to evaluate efficacy in vivo.

EXAMPLE 7

In Vitro Opsonophagocytosis Assays

Bacteria of ATCC 202176, a strain of *Staphylococcus* that carries the antigen, were transferred from stock beads to a new Tryptic soy agar plate. The plate was incubated for 18-20 hours at 3.7° C. in 5% $CO_2$. The bacteria were scraped from the plate and used for inoculation of 200 mL Columbia broth supplemented with 4% NaCl. Bacteria were incubated 18-20 hours at 37° C., then centrifuged at 2000 rpm for 10 minutes at 25-35° C., and supernatant was removed. The pelleted bacteria was resuspended in two milliliters of sterile saline, and used to prepare a suspension of bacteria of an optical density of 0.1 at 650 nm.

A 1:200 diluted sample prepared from the above-described bacterial suspension in MEM medium supplemented with 0.1% gelatin was used as working stock of bacteria solution. This bacterial preparation was tested against corresponding antisera for positive slide agglutination. The bacterial working stock was loaded into microtiter plate wells with the appropriate dilution of MEM medium.

PMNs were obtained from HL-60 cells adjusted to a concentration of $1.0 \times 10^6$ cells per ml in MEM medium supplemented with 0.1% gelatin. The PMN cells were centrifuged at 1000 rpm for 10 minutes at 30-35° C. The pelleted cells were resuspended in five milliliters of MEM medium supplemented with 0.1% gelatin, and centrifuged at 1000 rpm for 10 minutes. The pelleted cells were resuspended in one milliliter of MEM medium supplemented with 0.1% gelatin to yield a working concentration of $1 \times 10^6$/ml.

A human complement prepared from human serum was diluted to 1:80 in MEM medium supplemented with 0.1% gelatin. The reaction mixture in the microtiter plate wells contained 50 µl of bacteria [$10^6$ cells/ml], 50 µl of diluted sera, 50 µl PMN [$1\times10^6$ cells/ml] and 50 µl of complement [1:80], to give a total volume of 200 µl. At time zero, a 10 µl sample from the reaction plate was serially diluted 1:5, 1:10, and 1:50. A 10 µl sample from each dilution was plated onto a tryptic soy agar (TSA) plate. The TSA plates were incubated overnight 37° C., 5% $CO_2$. After the time zero dilution, the reaction plate was incubated at 37° C. for 90 minutes. The samples were remixed. A 10 µl sample from the reaction plate was serially diluted 1:5, 1:10, and 1:50. A 10 µl sample from each dilution was plated onto a TSA plates, which then were incubated overnight 37° C., 5% $CO_2$.

The bacterial colonies were counted for each dilution/sample/plate, and percentage kill of bacteria was calculated by the formula:

$$\% \text{ kill} = \frac{\text{No. of colonies at } T_0 - \text{no. of colonies at } T_{90} \times 100}{\text{number of colonies at } T_0}$$

Both whole cell antiserum from rabbits immunized with ATCC 202176 and rabbit antibodies raised against antigen-Dtd conjugates mediated the opsonophagocytosis of *Staphylococcus* by HL-60 in the presence of human complement. Opsonic activity of both whole cell antisera and anti-antigen-rEPA conjugate rabbit antibodies were absorbed out completely by antigen.

EXAMPLE 8

In Vivo Protection of Mice from Lethal *Staphylococcus* Challenge by Vaccination with Antigen-rEPA Conjugate A total of 24 mice were divided into three groups with 8 mice in each group. The mice in the first group were immunized with an intraperitoneal injection of 2.5 µg of purified antigen-rEPA conjugate produced according to Example 5 and IFA. The mice in the second group were injected with PBS plus IFA, while the mice in the third group were injected with PBS. The mice were boosted twice, at two week intervals, with the same vaccine or control dose.

One week after the third injection (second boost), the mice were challenged with $1.15\times10^8$ cfu of strain #V01048, a slime-producing strain of *S. epidermidis* that carries the antigen in 5% hog mucin. The challenged mice were monitored for morbidity and mortality. The results showed that 75% (⅔) of the mice in the first group survived lethal challenge, and were still alive at day 216 following challenge, while all mice in the second and third groups died by day 41 following challenge.

EXAMPLE 9

In Vivo Protection of Mice from Lethal *Staphylococcus* Challenge with Antigen-specific Monoclonal Antibody Prophylactic effect of antigen-specific monoclonal antibody was evaluated in the same mouse model using slime-producing *S. epidermidis* strain #977 that carries the antigen for the challenge. Groups of mice were immunized subcutaneously with either 0.5 mg or 1.0 mg of *S. epidermidis* antigen-specific monoclonal antibody, 1 mg of. *E. coli*-specific monoclonal antibody, or 1 mg of *S. epidermidis* slime-specific monoclonal antibody, respectively. Twenty-four hours after immunization, the mice were challenged intraperitoneally with $1\times10^8$ CFU of bacteria in 6% hog mucin and mice were monitored for morbidity and mortality. The results showed dose-dependent protection by monoclonal antibody specific to antigen according to the invention. Neither antibody specific to slime nor antibody specific to *E. coli* provided protection against challenge.

EXAMPLE 10

In Vivo Protection of Mice from Bacteremia by Vaccination with Antigen-Dtd Conjugate A total of 80 mice were divided into two groups with 40 mice in each group. The mice in the first group were immunized with a subcutaneous injection of 2.5 µg of purified antigen-Dtd conjugate produced according to Example 5 and IFA. The mice in the second group were injected with MEP conjugate (a conjugate of mucoid exopolysaccharide from *Pseudomonas aeruginosa* and Dtd) plus IFA. The mice were boosted twice, at two week intervals, with the same vaccine or control dose.

One week after the third injection the mice were challenged intraperitoneally with a sub-lethal dose ($5.0\times10^7$ cfu) of strain #V01048, a slime-producing strain of *S. epidermidis* that carries the antigen in 5% hog mucin. Challenged mice were exsanguinated and tested for positive bacterial cultures at 6, 24, 30 and 48 hours (ten mice at each time point). Results showed that immunization with antigen-rEPA conjugate significantly reduced bacteremia in the challenged mice, by facilitating clearance of bacteria from the blood. The control group immunized with the MEP conjugate were not protected against bacteremia.

EXAMPLE 11

Ability of Antigen to Block Adherence of *Staphylococcus* Bacteria to Intravenous Catheters In Vitro The ability of the antigen to mediate adherence of the slime-producing *S. epidermidis* strain #977 that carries the antigen and *S. haemolyticus* strain 4162 that carries the antigen (determined by double immunodiffusion of crude bacterial extract) to intravenous catheters was evaluated in an in vitro adherence assay. The bacteria were grown overnight at 37° C. on a Columbia agar plate supplemented with 4% sodium chloride. The following morning an isolated colony from this plate was inoculated into 5 ml of Columbia broth supplemented with 4% sodium chloride. This culture was then grown for 4 hours with shaking at 37° C. and then adjusted to an OD of 0.12 at 650 nM.

A single 1¼" IV Insyte catheter [Radiopaque Vialon® material, Becton Dickinson Vascular Access, Sandy, Utah] was incubated at 37° C. for 30 minutes in a 1 ml volume of a 0.5 mg/ml antigen solution in PBS. Catheters were then gently washed with cold PBS, immersed in 1 ml of bacterial suspension and incubated for 30 minutes at 37° C. without shaking. Catheters were then gently washed again with cold PBS solution and sliced into three even pieces. The sliced catheters were immersed in 500 µL of PBS and sonicated for 1 minute on ice to sonicate off catheter attached bacterial cells. This suspension was diluted to 1:10, 1:100, and 1:1000 in PBS and plated onto TSA plates and incubated 18-20 hours at 37° C. The bacterial colonies were counted, and differences in bacterial recovery from different antigen-coated catheters were determined.

Results showed that preincubation of the intravenous catheters with antigen isolated from S. epidermidis. 202176 reduced by 97.5% the adherence of the slime-producing S. epidermidis strain #977 that carries the antigen, and reduced by 92% the adherence of S. haemolyticus. The antigen identical to the antigen purified from S. epidermidis 202176 was detected in crude cell wall extracts of S. haemolyticus and S. hominis, suggesting that S. epidermidis antigen is responsible for adherence of coagulase-negative staphylococci to intravenous catheters.

EXAMPLE 12

Ability of Fab Fragments from Antigen-specific Antibodies to Block Adherence of Staphylococcus Bacteria to Intravenous Catheters In Vitro The ability of the Fab fragments prepared from antigen-specific antibodies to block adherence of the slime-producing S. epidermidis strain RP62A, a strain that carries the antigen, to intravenous catheter preincubated in human plasma was evaluated in and in vitro adherence assay. The bacteria was grown overnight at 37° C. on a Columbia agar plate supplemented with 4% sodium chloride. The following morning, an isolated colony from this plate was inoculated into 5 ml of Columbia broth supplemented with 4% sodium chloride. This culture was grown for 4 hours with shaking at 37° C. and then adjusted to an OD of 0.12 at 650 nm. Bacterial suspension (1 mL) was centrifuged at 3000 rpm and the pellet was resuspended in 1 mL of Fab solution (1 mg/mL) and incubated for 30 minutes at 37° C.

A single 1¼" IV Insyte catheter [Radiopaque Vialon® material, Becton Dickinson Vascular Access, Sandy, Utah] was incubated at 37° C. for 30 minutes in a 1 ml volume of a 0.5 mg/ml antigen solution in PBS. Catheters were then gently washed with cold PBS, immersed in 1 ml of bacterial suspension and incubated for 30 minutes at 37° C. without shaking. Catheters were then gently washed again with cold PBS solution and sliced into three even pieces. The sliced catheters were immersed in 500 µL of PBS and sonicated for 1 minute on ice to sonicate off catheter attached bacterial cells. This suspension was diluted to 1:10, 1:100, and 1:1000 in PBS and plated onto TSA plates and incubated 18-20 hours at 37° C. The bacterial colonies were counted, and differences in bacterial recovery from different antigen-coated catheters were determined.

Results showed that adherence of slime-producing S. epidermidis strain RP62A that carries the antigen was not affected by pretreatment of catheters with Fab fragments prepared from normal rabbit antibodies. Pretreatment of the same bacteria with Fab fragments prepared from antigen-specific rabbit antibodies effectively inhibited adherence of bacteria to the intravenous catheters. These data and data from Example 11 suggest that antigen plays an important role in adherence of coagulase-negative staphylococci to biomaterials. The inhibition of adherence by antigen and antigen-specific antibodies can play an important role in prevention of foreign body-related infections caused by coagulase-negative Staphylococcus.

What we claimed is:

1. An isolated hyperimmune globulin containing antibodies directed against a Staphylococcus epidermidis antigen that (a) comprises amino acids and a N-acetylated hexosamine in an α configuration, (b) contains no O-acetyl groups detectable by nuclear magnetic resonance spectroscopy, and (c) specifically binds with antibodies to a Staphylococcus epidermidis strain deposited under ATCC 202176.

2. An isolated monoclonal antibody directed against a Staphylococcus epidermidis antigen that (a) comprises amino acids and a N-acetylated hexosamine in an α configuration, (b) contains no O-acetyl groups detectable by nuclear magnetic resonance spectroscopy, and (c) specifically binds with antibodies to a Staphylococcus epidermidis strain deposited under ATCC 202176.

3. An isolated antibody directed against a Staphylococcus epidermidis antigen that (a) comprises amino acids and a N-acetylated hexosamine in an α configuration, (b) contains no O-acetyl groups detectable by nuclear magnetic resonance spectroscopy, and (c) specifically binds with antibodies to a Staphylococcus epidermidis strain deposited under ATCC 202176.

4. The isolated antibody of claim 3, wherein the antibody is a non-human antibody.

5. The isolated antibody of claim 3, wherein the antibody is a human antibody.

6. An immunotherapy method comprising a step of administering to a subjects:
an isolated hyperimmune globulin containing antibodies directed against a Staphylococcus epidermidis antigen that (a) comprises amino acids and a N-acetylated hexosamine in an α configuration, (b) contains no O-acetyl groups detectable by nuclear magnetic resonance spectroscopy, and (c) specifically binds with antibodies to a Staphylococcus epidermidis strain deposited under ATCC 202176;
an isolated monoclonal antibody directed against a Staphylococcus epidermidis antigen that (a) comprises amino acids and a N-acetylated hexosamine in an α configuration, (b) contains no O-acetyl groups detectable by nuclear magnetic resonance spectroscopy, and (c) specifically binds with antibodies to a Staphylococcus epidermidis strain deposited under ATCC 202176; or
an isolated antibody directed against a Staphylococcus epidermidis antigen that (a) comprises amino acids and a N-acetylated hexosamine in an α configuration, (b) contains no O-acetyl groups detectable by nuclear magnetic resonance spectroscopy, and (c) specifically binds with antibodies to a Staphylococcus epidermidis strain deposited under ATCC 202176.

7. The isolated hyperimmune globulin according to claim 1, the isolated monoclonal antibody according to claim 2, or the isolated antibody of claim 3, wherein the antigen comprises 2-acetamido-2-deoxy-α-D-glucopyranoside as said N-acetylated hexosamine is 2-acetamido-2-deoxy-α-D-glucopyranoside.

8. The isolated hyperimmune globulin according to claim 1, the isolated monoclonal antibody according to claim 2, or the isolated antibody of claim 3, wherein the antigen comprises the amino acids serine, alanine, aspartic acid/asparagine, valine, and threonine.

9. The isolated hyperimmune globulin according to claim 1, the isolated monoclonal antibody according to claim 2, or the isolated antibody of claim 3, wherein the antigen comprises the amino acids serine, alanine, aspartic acid/asparagine, valine, and threonine in a molar ratio of approximately 39:25:16:10:7, respectively.

10. The isolated hyperimmune globulin according to claim 1, the isolated monoclonal antibody according to claim 2, or the isolated antibody of claim 3, wherein the antigen is conjugated to an immunocarrier.

11. The isolated hyperimmune globulin according to claim 1, the isolated monoclonal antibody according to claim 2, or the isolated antibody of claim 3, wherein the antigen is conjugated to an immunocarrier that is a recombinantly-produced, non-toxic mutant strain of *Pseudomonas aeruginosa* exotoxin A.

12. A kit for detecting the presence of anti-*Staphylococcus epidermidis* antibody in a sample, comprising:
   an isolated monoclonal antibody directed against a *Staphylococcus epidermidis* antigen that (a) comprises amino acids and a N-acetylated hexosamine in an α configuration, (b) contains no O-acetyl groups detectable by nuclear magnetic resonance spectroscopy, and (c) specifically binds with antibodies to a *Staphylococcus epidermidis* strain deposited under ATCC 202176; and
   instructions for mixing said monoclonal antibody with a sample suspected of containing *Staphylococcus epidermidis*-specific antigen and monitoring said mixture for binding between said monoclonal antibody and *Staphylococcus epidermidis*-specific antigen in said sample.

13. A kit as claimed in claim 12, wherein said isolated monoclonal antibody is immobilized on a solid matrix.

* * * * *

UNITED STATES PATENT AND TRADEMARK OFFICE
CERTIFICATE OF CORRECTION

| | | |
|---|---|---|
| PATENT NO. | : 7,531,633 B2 | Page 1 of 1 |
| APPLICATION NO. | : 11/014997 | |
| DATED | : May 12, 2009 | |
| INVENTOR(S) | : Pavliak et al. | |

It is certified that error appears in the above-identified patent and that said Letters Patent is hereby corrected as shown below:

On the title page,

[*] Notice: Subject to any disclaimer, the term of this patent is extended or adjusted under 35 USC 154(b) by 509 days.

Delete the phrase "by 509 days" and insert -- by 883 days --

Signed and Sealed this

Eighteenth Day of May, 2010

David J. Kappos
*Director of the United States Patent and Trademark Office*